(12) United States Patent
Lan et al.

(10) Patent No.: US 10,124,323 B2
(45) Date of Patent: Nov. 13, 2018

(54) NANO-NICKEL CATALYST AND HYDROGENATION DEVICE OF CARBON OXIDES

(71) Applicant: NATIONAL CHENG KUNG UNIVERSITY, Tainan (TW)

(72) Inventors: Po-Wei Lan, Tainan (TW); Cheng-Wei Huang, Tainan (TW); Yu-Wen Hou, Tainan (TW); Chen-Chien Wang, Tainan (TW); Chuh-Yung Chen, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 15/828,709

(22) Filed: Dec. 1, 2017

(65) Prior Publication Data
US 2018/0178200 A1 Jun. 28, 2018

Related U.S. Application Data

(60) Provisional application No. 62/438,369, filed on Dec. 22, 2016.

(30) Foreign Application Priority Data

Sep. 6, 2017 (TW) .............................. 106130511 A

(51) Int. Cl.
*B01J 23/755* (2006.01)
*B01J 35/08* (2006.01)
(Continued)

(52) U.S. Cl.
CPC ............. *B01J 23/755* (2013.01); *B01J 35/08* (2013.01); *B01J 35/1009* (2013.01);
(Continued)

(58) Field of Classification Search
CPC ...... B01J 23/755; B01J 35/08; B01J 35/1009; B01J 35/1038; C10G 2/33; C10G 2/341
See application file for complete search history.

(56) References Cited

U.S. PATENT DOCUMENTS 6,309,758 B1 * 10/2001 Schmidt .................. B01J 25/00
427/305
7,375,053 B2 * 5/2008 Schmidt .................. B01J 25/00
502/313

(Continued)

FOREIGN PATENT DOCUMENTS

CN 104084219 A 10/2014
WO 2013063064 A1 5/2013

OTHER PUBLICATIONS

Lixia Sun et al. "Magnetic Field Effects on the Formation and Properties of Nickel Nanostructures", European Journal of Inorganic Chemistry, Jan. 1, 2009; pp. 435-440, chemische berichte, wiley-vch verlag, weinheim, DE, vol. 2009, No. 3, XP009504393.

(Continued)

*Primary Examiner* — Cam N. Nguyen
(74) *Attorney, Agent, or Firm* — Muncy, Geissler, Olds & Lowe, P.C.

(57) ABSTRACT

A nano-nickel catalyst and a hydrogenation device of carbon oxides are provided. The hydrogenation device is configured to reduce the carbon oxides to form low carbon hydrocarbons. The nano-nickel catalyst has a metallic nickel body and a plurality of microstructures connecting with at least one surface of the metallic nickel body. The microstructures are sharp, and have a length-diameter ratio ranging from 2 to 5.

13 Claims, 3 Drawing Sheets

(51) Int. Cl.
*B01J 35/10* (2006.01)
*C10G 2/00* (2006.01)

(52) U.S. Cl.
CPC ............ *B01J 35/1038* (2013.01); *C10G 2/33* (2013.01); *C10G 2/341* (2013.01); *B01J 2231/625* (2013.01); *B01J 2523/847* (2013.01)

(56) References Cited

U.S. PATENT DOCUMENTS

| | | | | |
|---|---|---|---|---|
| 8,034,152 | B2* | 10/2011 | Westin | B01J 23/755 75/235 |
| 8,298,985 | B2* | 10/2012 | Morgenstern | B01J 23/72 420/89 |
| 8,399,527 | B1* | 3/2013 | Brown | C10G 2/332 518/700 |
| 9,050,591 | B2* | 6/2015 | Fraga-Dubreuil | B01J 31/1845 |
| 9,486,789 | B2* | 11/2016 | Decottignies | B01J 27/1853 |
| 9,512,365 | B2* | 12/2016 | Decottignies | C10G 2/33 |
| 2009/0203518 | A1* | 8/2009 | Dalton | B01J 23/755 502/159 |
| 2011/0011772 | A1* | 1/2011 | Schmidt | B01J 23/74 208/244 |
| 2014/0194279 | A1* | 7/2014 | Young | H01M 4/242 502/185 |
| 2014/0194282 | A1* | 7/2014 | Young | H01M 4/383 502/337 |
| 2016/0059219 | A1 | 3/2016 | Chen et al. | |
| 2017/0282147 | A1 | 10/2017 | Shen et al. | |

OTHER PUBLICATIONS

Gun Dae Lee et al.; "Raney Ni Catalysts Derived from Different Alloy Precursors Part II. CO and CO2 Methanation Activity", Korean Journal of Chemical Engineering; Jul. 31, 2005: pp. 541-546; vol. 1. 22, No. 4, XP055470207.

* cited by examiner

NANO-NICKEL CATALYST AND HYDROGENATION DEVICE OF CARBON OXIDES

CROSS REFERENCE TO RELATED APPLICATIONS

This application claims the benefit of the filing date of U.S. provisional patent application Ser. No. 62/438,369, filed on Dec. 22, 2016, and Taiwan patent application No. 106130511, filed on Sep. 6, 2017, the disclosures of which are incorporated herein by reference in their entirety.

FIELD OF THE DISCLOSURE

The present disclosure relates to a nano-nickel catalyst and a hydrogenation device of carbon oxides, and particularly relates to a nano-nickel catalyst with sharp microstructures and a hydrogenation device of carbon oxides using the nano-nickel catalyst.

BACKGROUND OF THE DISCLOSURE

Because environmental issues are increasingly being taken into account, greenhouse effect, mainly caused by carbon dioxide, is especially in particular need of improvement. It will be very helpful to improve environmental problems by providing a material that can convert carbon dioxide-containing gas, such as exhaust gas or flue gas discharged from a factory, into an economically valuable substance.

Conventionally, for increasing contact opportunity of a catalyst and reactants, particle size of the catalyst is minimized to increase its surface area. The minimized catalyst can be applied to part of industrial processes (e.g. Catalytic Cracking Reaction System in the petroleum industry). But in general, a catalyst having too small of a particle size is inconvenient to use. Therefore, in the industrial process, the particle size of the catalyst is formed larger in the shape of balls or cylinders. It is also possible to fill the catalyst in a tube to form a fixed bed reactor. However, a considerable pressure drop will occur when fluid passes through the fixed bed reactor. This phenomenon is more significant when the catalyst has smaller particle size and the flow rate of the fluid increases. Therefore, it is necessary to increase the pressure to push the gaseous reactants to pass the catalyst bed, and thus the fixed bed reactor is not suitable for treating large amounts of exhaust gas.

Chen et al. discloses a hydrogenation catalyst in U.S. Pat. No. 9,433,932 having a nanonickel carrier, and noble metal nanoparticles selected from Pd, Pt, Ru, Rh, or a mixture thereof, which are mounted onto the nanonickel carrier. The hydrogenation catalyst is advantageous for catalyzing hydrogenation of an aqueous compound with a benzene ring. However, the hydrogenation catalyst disclosed by Chen is a one-dimensional nanonickel carrier (nano-wire), it is not good for the staking use of the nano-wire catalyst. In addition, the hydrogenation catalyst does not show an activity for reducing carbon dioxide, and an ability of converting carbon oxides into a low carbon hydrocarbons.

It is therefore necessary to provide a nano-nickel catalyst and a hydrogenation device for treating carbon dioxide efficiently, in order to solve the problems existing in the conventional technology as described above.

SUMMARY OF THE DISCLOSURE

In view of this, a primary object of the present disclosure is to provide a nano-nickel catalyst having special microstructures thereon for increasing a specific surface area of the catalyst, and maintain a specific distance between each other. When stacking a large amount of the nano-nickel catalyst, it is possible to create channels between the catalysts for passing reactants, and thus the contact area between the reactants and the catalyst is increased to improve the reaction efficiency and the conversion rate. Furthermore, the nano-nickel catalyst of the present disclosure is particularly advantageous for forming a catalyst bed for the catalytic reaction of gas reactants.

Another object of the present disclosure is to provide a hydrogenation device of carbon oxides by using abovementioned nano-nickel catalyst filled in a reactor as a hydrogenation catalyst to convert carbon dioxide or carbon monoxide into a low-carbon hydrocarbons such as methane, ethane, or propane. In addition, it is possible to connect a plurality of reactors in series to improve the conversion rate of the hydrogenation reaction, or use different reaction conditions in different reactors to obtain the required products.

It is still another object of the present disclosure to provide a hydrogenation method of carbon oxides. A hydrogenation reaction of carbon monoxide (CO)/carbon dioxide ($CO_2$) is carried out by using a catalyst bed formed by the abovementioned nano-nickel catalyst, in order to produce CO, methane ($CH_4$), ethane ($C_2H_5$), or propane ($C_3H_8$). The hydrogenation method of the carbon oxides has the advantages of a high conversion rate and a high yield, and can be carried out in atmospheric pressure. Thus, it is very advantageous for treatment of a large amount treatment of carbon dioxide.

To achieve the above objects, the present disclosure provides a nano-nickel catalyst, comprising a metallic nickel body; and a plurality of microstructures connecting to the metallic nickel body on at least one surface of the metallic nickel body; wherein the microstructures are sharp, and have a length-diameter ratio ranging from 2 to 5.

In one embodiment of the present disclosure, the microstructures contain metallic nickel.

In one embodiment of the present disclosure, the microstructures are made of metallic nickel.

In one embodiment of the present disclosure, the metallic nickel body is spherical.

In one embodiment of the present disclosure, the metallic nickel body is porous.

In one embodiment of the present disclosure, the metallic nickel body is solid.

In one embodiment of the present disclosure, the metallic nickel body is hollow.

In one embodiment of the present disclosure, the metallic nickel body is porous, and has an adsorption pore volume ranging from 0.0024 $cm^3/g$ to 0.0062 $cm^3/g$.

In one embodiment of the present disclosure, the nano-nickel catalyst has a specific surface area ranging from 1.5 $m^2/g$ to 2.0 $m^2/g$.

In one embodiment of the present disclosure, the nano-nickel catalyst has an ability to reduce carbon oxides into low-carbon hydrocarbons.

In one embodiment of the present disclosure, the carbon oxides are carbon monoxide or carbon dioxide.

In one embodiment of the present disclosure, the low-carbon hydrocarbons are selected from a group consisting of methane, ethane, propane, and a combination thereof.

To achieve above objects, another embodiment of the present disclosure provides a hydrogenation device of carbon oxides, comprising a first reactor having a first catalyst bed therein; and a second reactor having a second catalyst bed therein, and communicated with the first reactor through a channel; wherein the first catalyst bed and the second catalyst bed both comprise the abovementioned nano-nickel catalyst.

In one embodiment of the present disclosure, the first catalyst bed has a first catalyst fill rate with a minimum value of 0.3 g/ml, and the second catalyst bed has a second catalyst fill rate with a minimum value of 0.15 g/ml.

To achieve above objects, a further embodiment of the present disclosure provides a hydrogenation method of carbon oxides, comprising steps of: (1) performing a first hydrogenation reaction on carbon oxides and hydrogen under a first catalyst bed to form a first gas mixture, wherein the first catalyst bed comprises the abovementioned nano-nickel catalyst.

In one embodiment of the present disclosure, the first hydrogenation reaction is carried out at a temperature T1 ranging from 180° C. to 250° C.

In one embodiment of the present disclosure, in the step (1), a flow rate of the carbon oxides is 7.2 ml/min; a flow rate of the hydrogen is 30 ml/min.

In one embodiment of the present disclosure, the hydrogenation method further comprises a step of (2) performing a second hydrogenation reaction on the first gas mixture and hydrogen under a second catalyst bed to form a low-carbon hydrocarbons mixture stream, wherein the second catalyst bed comprises the abovementioned nano-nickel catalyst.

In one embodiment of the present disclosure, the second hydrogenation reaction is carried out at a temperature T2 ranging from 600° C. to 800° C.

In one embodiment of the present disclosure, in the step (2), a flow rate of the carbon oxide is 7.2 ml/min; a flow rate of the hydrogen is 30 ml/min.

In one embodiment of the present disclosure, before the step (1), the hydrogenation method further comprises a step of heating the first catalyst bed and the second catalyst bed in hydrogen to 250° C. to perform a reduction reaction on the first catalyst bed and the second catalyst bed.

In one embodiment of the present disclosure, the step (1) comprises mixing an inert gas, the carbon oxides, and the hydrogen to form a reaction stream.

In one embodiment of the present disclosure, the inert gas is nitrogen or argon.

In one embodiment of the present disclosure, the first gas mixture comprises methane and carbon monoxide.

In one embodiment of the present disclosure, the low-carbon hydrocarbons mixture stream is selected from methane, ethane, propane, or a combination thereof.

DETAILED DESCRIPTION OF THE PREFERRED EMBODIMENTS

The structure and the technical means adopted by the present disclosure to achieve the above and other objects can be best understood by referring to the following detailed description of the preferred embodiments. Furthermore, if there is no specific description in the disclosure, singular terms such as "a", "one", and "the" include the plural number. For example, "a compound" or "at least one compound" may include a plurality of compounds, and the mixtures thereof. If there is no specific description in the disclosure, "%" means "weight percentage (w.t. %)", and the numerical range (e.g., 10%-11% of A) contains the upper and lower limit (i.e., 10%≤A≤11%). If the lower limit is not defined in the range (e.g., less than, or below 0.2% of B), it means that the lower limit may be 0 (i.e., 0%≤B≤0.2%). The proportion of "weight percent" of each component can be replaced by the proportion of "weight portion" thereof. The abovementioned terms are used to describe and understand the present disclosure, but the present disclosure is not limited thereto.

Figure 1A:
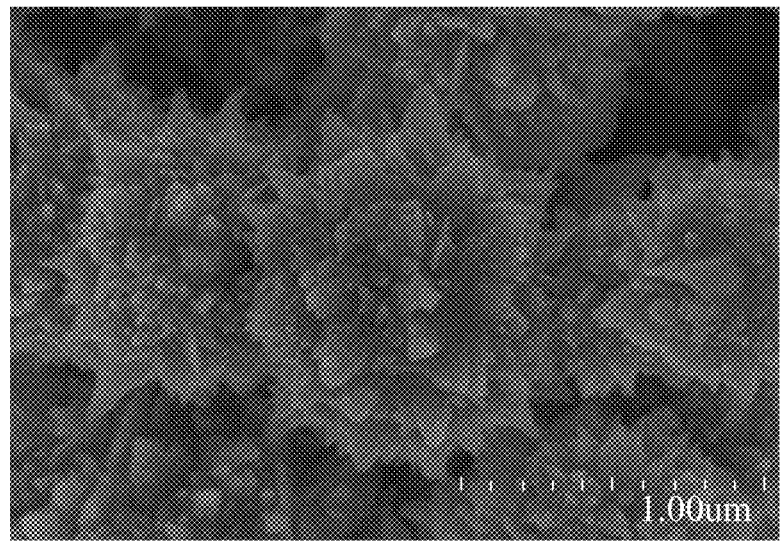
FIGS. 1A-1B are photos of a nano-nickel catalyst observed by scanning electron microscope (SEM) according to one embodiment of the present disclosure.
Figure 1B:
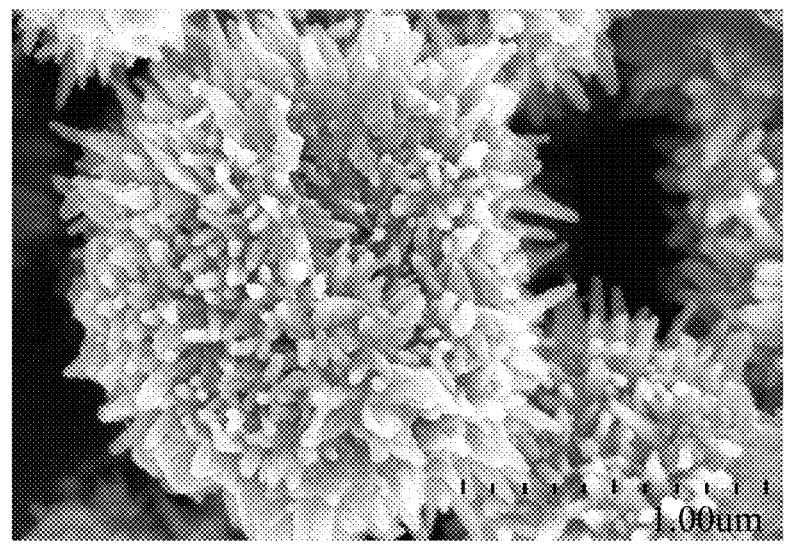

Firstly, one embodiment of the present disclosure provides a nano-nickel catalyst used for catalyze a hydrogenation reaction of carbon oxides. The nano-nickel catalyst has a metallic nickel body; and a plurality of microstructures connecting to the metallic nickel body on at least one surface of the metallic nickel body. The microstructures are sharp, and have a length-diameter ratio ranging from 2 to 5, such as 2.5, 3.0, or 4.5, but it is not limited thereto. As shown in FIG. 1A and FIG. 1B, the nano-nickel catalysts have various sharp microstructures. The nano-nickel catalyst in FIG. 1A is formed in a magnetic field, but the nano-nickel catalyst in FIG. 1B is not.

In one embodiment of the present disclosure, the microstructures mainly contain metallic nickel. That is, the metallic nickel body and the microstructures can be formed simultaneously. It is also possible that the microstructures are attached on the surface of the metallic nickel body after the metallic nickel body is formed. Alternatively, the microstructures contain other components, such as precious metals, and the components can be used for modifying the microstructures to achieve the required catalysis reaction. In addition to increasing the total surface area of the nano-nickel catalyst, the main function of the microstructures is to maintain a distance between the nano-nickel catalysts when a plurality of the nano-nickel catalysts are filled within a container, so that the nano-nickel catalysts form pores or channels between each other to allow the contact area between the reactant and the nano-nickel catalyst to increase during the reaction and to promote the efficiency of the catalysis reaction. Preferably, the nano-nickel catalyst has a catalyst fill rate ranging from 3.0 g/cm$^3$ to 8.0 g/cm$^3$, preferably 3.33 g/cm$^3$ to 7.59 g/cm$^3$.

Furthermore, in one embodiment of the present disclosure, the metallic nickel body is substantially spherical. Preferably, the metallic nickel body is porous, solid, or hollow. Preferably, the metallic nickel body is porous, and has an adsorption pore volume ranging from 0.0024 cm$^3$/g to 0.0062 cm$^3$/g, which allows most of the reactants to contact the surface of the nano-nickel catalyst rather than go through the inside of the metallic nickel body to react. Preferably, the nano-nickel catalyst has a specific surface area ranging from 1.5 m$^2$/g to 2.0 m$^2$/g. In addition, the nano-nickel catalyst has an ability to reduce carbon oxides into low-carbon hydrocarbons. The carbon oxides are carbon monoxide and/or carbon dioxide. The low-carbon hydrocarbons are selected from a group consisting of methane, ethane, propane, and a combination thereof.

Figure 2:
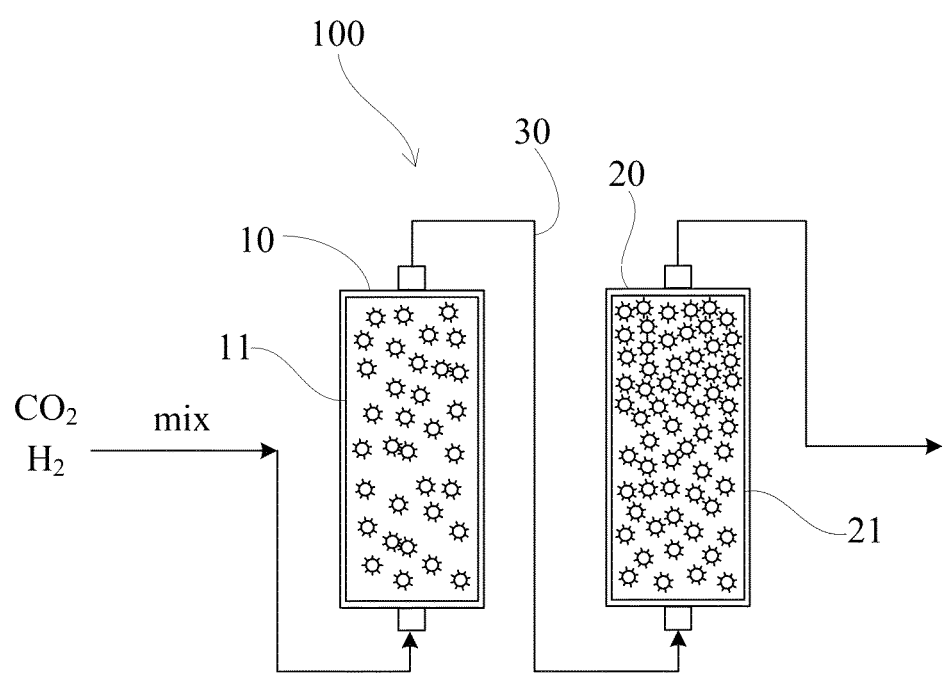
FIG. 2 is a schematic view of a hydrogenation device of carbon oxides according to one embodiment of the present disclosure.

Referring to FIG. 2, another embodiment of the present disclosure provides a hydrogenation device of carbon oxides 100, comprising a first reactor 10 having a first catalyst bed 11 therein; and a second reactor 20 communicated with the first reactor through a channel 30. The second reactor 20 has a second catalyst bed 21 therein. The first catalyst bed and the second catalyst bed both comprise the abovementioned nano-nickel catalyst. In one embodiment of the present disclosure, the first catalyst bed has a first catalyst fill rate with a minimum value of 0.3 g/ml, and the second catalyst bed has a second catalyst fill rate with a minimum value of 0.15 g/ml. Therefore, the first catalyst bed and the second catalyst bed can catalyze the react with a very small amount of the catalyst.

A further embodiment of the present disclosure provides a hydrogenation method of carbon oxides, comprising steps of (S1) performing a first hydrogenation reaction on carbon oxides and hydrogen under a first catalyst bed to form a first gas mixture; and (S2) performing a second hydrogenation reaction on the first gas mixture and hydrogen under a second catalyst bed to form a low-carbon hydrocarbons mixture stream. The first catalyst bed and the second catalyst bed both comprises the abovementioned nano-nickel catalyst.

Firstly, referring to FIG. 2 again, the hydrogenation method of the carbon oxides according to one embodiment of the present disclosure comprises a step of (S1) performing a first hydrogenation reaction on carbon oxides and hydrogen under a first catalyst bed 11 to form a first gas mixture. In this step, the carbon oxides can be carbon dioxide, carbon monoxide, or a mixture thereof. The first hydrogenation reaction is for example carried out in the first reactor 10, and at a first temperature T1 ranging from 180° C. to 250° C., such as 180° C., 200° C., 210° C., 220° C., 230° C., 240° C., or 250° C., but it is not limited thereto. A flow rate of the carbon oxides within the first reactor is 2-7.2 ml/min; and a flow rate of the hydrogen within the first reactor is 30-33 ml/min. Preferably, in this step, the method further comprises a step of mixing an inert gas, the carbon oxides, and the hydrogen to form a reaction stream. The inert gas can be nitrogen or argon. The first gas mixture comprises methane, and further comprises water vapor; hydrogen or carbon dioxide which are not reacted completely; or carbon monoxide.

Next, the hydrogenation method of the carbon oxides according to one embodiment of the present disclosure comprises a step of (S2) performing a second hydrogenation reaction on the first gas mixture and hydrogen under a second catalyst bed 21 to form a low-carbon hydrocarbons mixture stream. In this step, the second hydrogenation reaction is carried out at a second temperature T2 ranging from 600° C. to 800° C. A flow rate of the carbon oxides within the second reactor is 2-7.2 ml/min; and a flow rate of the hydrogen within the second reactor is 30-33 ml/min. Preferably, since the first reactor 10 and the second reactor 20 can be communicated through the channel 30, the first reactor 10 and the second reactor have substantially same flow rate. However, the hydrogenation device of the present disclosure is not limited to what is mentioned above, it is also possible to use additional apparatus, such as condensing tubes, flow valves, or any means for facilitating monitoring and control of the reaction. Thus, the hydrogen and the carbon oxides within the first reactor 10 and the second reactor 20 can have different flow rates, respectively. In one embodiment of the present disclosure, the low-carbon hydrocarbons mixture stream can be one or more of methane, ethane, and propane.

Moreover, although the hydrogenation method of carbon oxides in the present disclosure does not need to provide additional hydrogen in the step (S2), additional hydrogen can be added in the step (S2) depending on the reaction conditions.

Preferably, in one embodiment of the present disclosure, before the step (S1), the hydrogenation method further comprises a step of heating the first catalyst bed 11 and the second catalyst bed 21 in hydrogen to 250° C. to perform a reduction reaction on the first catalyst bed 11 and the second catalyst bed 21. After the reduction reaction, the nano-nickel catalyst have better activity for catalysis.

In order to verify the reaction efficiency of the nano-nickel catalyst of the present disclosure, several experiments were carried out as follows.

Experiment 1: Preparation of a Nano-Nickel Catalyst (1) preparing an aqueous solution containing nickel ions; (2) adding a reducing agent in the aqueous solution containing nickel ions to form a reactant solution, and the reducing agent can be hydrazine; (3) applying a magnetic field to the reactant solution for a first duration to obtain a nano-nickel catalyst. The aqueous solution containing nickel ions in the step (1) is prepared from nickel chloride and deionized water. The aqueous solution containing nickel ions can further comprise an assistant agent selected from carboxymethyl cellulose, sodium citrate, sodium hydroxide, or a mixture thereof. The carboxymethyl cellulose is preferred 0.1-1 w.t. % of the aqueous solution containing nickel ions. The step (1) can further comprises a step (1a) of heating and stirring until the assistant agent is totally dissolved in the aqueous solution containing nickel ions. The compounds used in the experiment 1 and the reaction condition are shown in Table 1.

TABLE 1

| $H_2O$ (parts) | nickel chloride (parts) | sodium citrate (parts) | NaOH (parts) | Hydrazine (parts) | carboxymethyl cellulose (parts) | Temp. (° C.) | Time (hrs) |
| --- | --- | --- | --- | --- | --- | --- | --- |
| 80 | 9.3 | 13 | 2.8 | 9 | 0.08-0.8 | 75 | 6-8 |

Figure 3A:
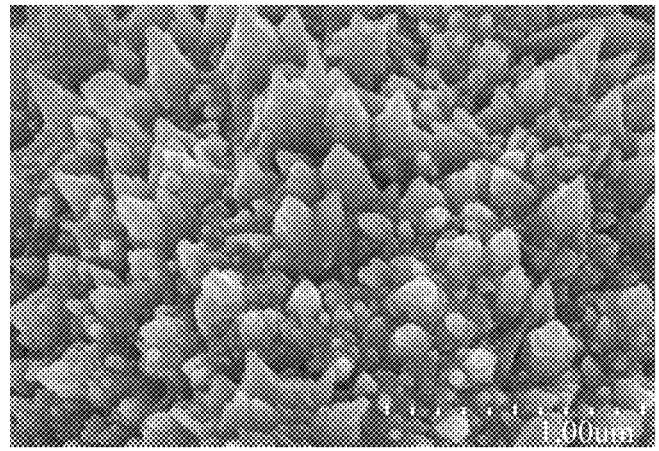
FIGS. 3A-3B are photos of a nano-nickel catalyst observed by scanning electron microscope (SEM) in experiment 1 of the present disclosure.
Figure 3B:
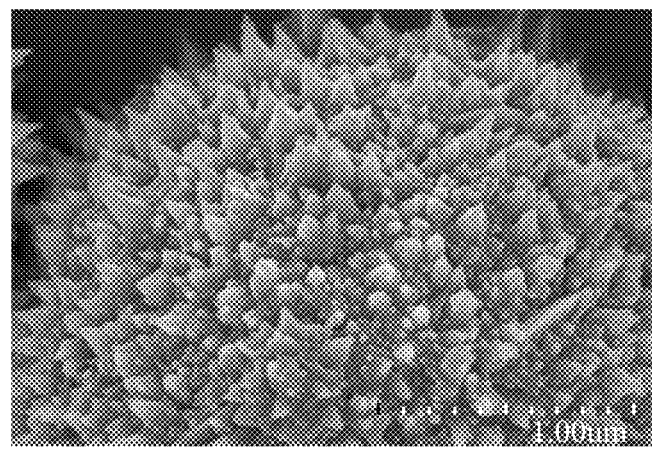

Next, under an applied magnetic field, the position of the magnet was changed, that is, the magnetic arrangement was also changed. Nickel chloride was used as a precursor and a nucleating agent was introduced into the aqueous solution. A reduction reaction was performed by adding a reducing agent, and then the nickel nanocrystal can be formed and self-assembled into a spherical structure with specific microstructures on the surface of the spherical structure. For example, 8 pieces of magnet can be divided into 2 sets, and placed around the reactor on a lower layer and an upper layer. The nano-nickel catalyst having specific microstructures as shown in FIGS. 3A and 3B can be obtained when the reaction was completed.

Experiment 2: Hydrogenation of Carbon Dioxide

The nano-nickel catalyst obtained in Experiment 1 was filled in the first reactor 10 and the second reactor 20 as shown in FIG. 2, and the first hydrogenation reaction and the second hydrogenation reaction were carried out at various temperatures. The experimental conditions were as follows:

Experiment 2-1

The main reaction of the first hydrogenation reaction is as follows:

$$CO_2 + 4H_2 \rightarrow CH_4 + 2H_2O$$

The reaction conditions in the first hydrogenation reaction are: $H_2$=30 cc/min; $CO_2$=7.2 cc/min; $N_2$=5 cc/min; $H_2/CO_2$=4.2; volume of the first catalyst bed=50 ml; 35 g of the nano-nickel catalyst. The conversion rates of each component in the first hydrogenation reaction are shown in Table 2.

TABLE 2

| Temp (° C.) | $CO_2$ conversion | $H_2$ conversion | Consumption ratio $H_2/CO_2$ |
| --- | --- | --- | --- |
| 180 | 71.6% | 68.6% | 4.0 |
| 190 | 97.6% | 92.8% | 4.0 |
| 200 | 99.4% | 94.8% | 4.0 |
| 210 | 100% | 94.9% | 4.0 |
| 225 | 100% | 94.4% | 3.9 |

Form Table 2, it can be observed that the higher the reaction temperature of the first hydrogenation reaction, the higher the conversion rate of carbon dioxide and hydrogen. It can also be understood that the first hydrogenation reaction is carried out very completely.

Experiment 2-2: Preparation of Methane

Next, the reaction conditions of the first hydrogenation reaction are modified, in which: $H_2$=32 cc/min; $CO_2$=5 cc/min; $H_2/CO_2$=6.4; the first catalyst bed=75 ml; and 90 g of the nano-nickel catalyst. The conversion of the first hydrogenation reaction is shown in Table 3.

TABLE 3

| Temp (° C.) | $CO_2$ Conversion | $H_2$ conversion | Consumption ratio $H_2/CO_2$ | $CH_4$ selectivity | $C_2H_6$ selectivity |
| --- | --- | --- | --- | --- | --- |
| 160 | 33.9% | 27.5% | 5.2 | 100% | / |
| 170 | 77.5% | 58.7% | 4.8 | 99.9% | 0.1% |
| 180 | 100% | 63.2% | 4.0 | 99.9% | 0.1% |
| 200 | 100% | 63.1% | 4.0 | 99.9% | 0.1% |

From Table 3, the higher the reaction temperature, the conversion rates of the $CO_2$ and $H_2$ are increased, and the consumption ratio of $H_2$ is lowered. Thus, the cost can be reduced and the reaction efficiency can be promoted, so as to produce large amounts of methane and small amounts of ethane. From Table 2 and Table 3, it can be understood that the preferred temperature for forming methane or propane form $CO_2$ is above 180° C.

Experiment 2-3: Preparation of Carbon Monoxide

The main reaction for the preparation of carbon monoxide (CO) is as follows:

$$CH_4 + H_2O \rightarrow CO + 3H_2$$

For testing the efficiency of continuous execution of the first hydrogenation and the second hydrogenation, 45 g of the nano-nickel catalyst obtained in Experiment 1 was filled in the first reactor 10 having a diameter of 1 cm and a height of 100 cm; and 180 g of the nano-nickel catalyst obtained in Experiment 1 was filled in the second reactor 20 having a diameter of 2.54 cm and a height of 120 cm.

First, the hydrogen was introduced and two reactors were heated to 250° C. to reduce the catalyst for 1 hour. Next, the hydrogen, $CO_2$, and $N_2$ were introduced for 2 hours to allow the reactors and the channel(s) to have a consistent gas environment. Next, the first reactor 10 was heated to 225° C., and the analysis sample was collected by a gas chromatograph (GC) at the outlet of the second reactor 20 to ensure the complete conversion of $CO_2$. Next, the second reactor 20 was heated to 600-800° C. and the reaction condition was observed. The results were shown in Table 4.

TABLE 4

| Temp. (° C.) | $CH_4$(%) | CO(%) | $CO_2$(%) |
| --- | --- | --- | --- |
| 650 | 4.5 | 54.6 | 40.9 |
| 675 | 2.5 | 62.7 | 34.8 |
| 700 | 3.2 | 68.0 | 28.9 |
| 725 | 2.3 | 68.0 | 29.7 |

From Table 4, it can be found that the proportion of $CO_2$ is smaller, the formation of CH4 is decreased, but the formation of CO is increased when the reaction temperature in the second reactor is increased. It can be understood that the CH4 generated through the first reactor has been consumed to generate large amount of CO. In addition, the first reactor (at the lower temperature 225° C.) and the second reactor (at the higher temperature 600-800° C.) both use same nano-nickel catalyst, but the temperatures can be modified, respectively, to obtain the required amount of CO or $CH_4$.

Experiment 2-4: Preparation of Low-Carbon Hydrocarbons ($C_2H_6$ and $C_3H_8$)

In order to demonstrate that the nano-nickel catalyst of the present disclosure has abilities to convert carbon monoxide to methane, ethane, or propane, the nano-nickel catalyst obtained in Experiment 1 was filled in a reactor (e.g., the first reactor 10 or the second reactor 20 shown in FIG. 2), and the reaction stream containing $H_2$, CO, and $N_2$ was directly introduced into the reactor. The product stream was gathered at the outlet of the reactor for analysis. The experimental conditions and results are shown in Table 5.

TABLE 5

| Flow rate of the reaction stream (cc/min) | | | Temp. (° C.) | CO Conversion (mol %) | Product stream | | | | |
| --- | --- | --- | --- | --- | --- | --- | --- | --- | --- |
| $H_2$ | CO | $N_2$ | | | CO (mol %) | $CO_2$ (mol %) | $CH_4$ (mol %) | $C_2H_6$ (mol %) | $C_3H_8$ (mol %) |
| 35 | 5.2 | — | 160 | 63.4 | 47.2 | 2.3 | 31.6 | 9.0 | 9.9 |
| 35 | 5.2 | — | 170 | 93.6 | 9.0 | 4.2 | 58.5 | 15.1 | 13.2 |
| 35 | 5.2 | — | 180 | 100 | — | — | 75.4 | 14.6 | 10.0 |

TABLE 5-continued

| Flow rate of the reaction stream (cc/min) | | | Temp. | CO Conversion | Product stream | | | | |
|---|---|---|---|---|---|---|---|---|---|
| | | | | | CO | CO₂ | CH₄ | C₂H₆ | C₃H₈ |
| H₂ | CO | N₂ | (° C.) | (mol %) | (mol %) | (mol %) | (mol %) | (mol %) | (mol %) |
| 35 | 5.2 | — | 200 | 100 | — | — | 93.7 | 6.3 | — |
| 30 | 5.2 | 5 | 160 | 90.5 | 12.3 | 3 | 58.5 | 15.3 | 10.8 |
| 30 | 5.2 | 5 | 170 | 100 | — | — | 81.8 | 14.5 | 3.7 |
| 30 | 5.2 | 5 | 180 | 100 | — | — | 96.1 | 3.9 | — |
| 30 | 5.2 | 5 | 200 | 100 | — | — | 100 | — | — |
| 33 | 5.2 | — | 160 | 69.4 | 40.8 | 4.0 | 33.4 | 10.3 | 11.5 |
| 33 | 5.2 | — | 170 | 100 | — | — | 71.9 | 14.4 | 13.7 |
| 33 | 5.2 | — | 180 | 100 | — | — | 82.0 | 14.1 | 3.9 |
| 33 | 5.2 | — | 200 | 100 | — | — | 98.5 | 1.5 | — |
| 30 | 8.2 | — | 160 | 43.7 | 67.1 | 2.6 | 18.1 | 5.4 | 6.8 |
| 30 | 8.2 | — | 170 | 71.5 | 37.6 | 4.5 | 37.2 | 9.1 | 11.5 |
| 30 | 8.2 | — | 180 | 100 | — | 5.9 | 70.2 | 15.6 | 8.3 |
| 30 | 8.2 | — | 200 | 100 | — | 13.5 | 86.5 | — | — |

From Table 5, it can be understood that the nano-nickel catalyst of the present disclosure can be served as a hydrogenation catalyst of CO/CO₂ to directly convert CO/CO₂ into methane, ethane, or propane. Depending on various objects, the reaction conditions can be modified, such as flow rate, temperature, or reactant ratio. It is also possible to use a plurality of reactors in series to do hydrogenation reaction continuously and obtain the required products. In addition, a fairly good methane conversion can be achieved at atmospheric pressure by using the nano-nickel catalyst of the present disclosure, there is no need to react at a relative high temperature. This will not only save energy, but also reduce the requirement of the reaction conditions.

The present disclosure has been described with preferred embodiments thereof and it is understood that many changes and modifications to the described embodiments can be carried out without departing from the scope and the spirit of the disclosure that is intended to be limited only by the appended claims.

What is claimed is:

1. A nano-nickel catalyst, comprising:
    a metallic nickel body; and
    a plurality of microstructures connected to the metallic nickel body on at least one surface of the metallic nickel body;
    wherein the microstructures are sharp, and have a length-diameter ratio ranging from 2 to 5.

2. The nano-nickel catalyst according to claim 1, wherein the microstructures contain metallic nickel.

3. The nano-nickel catalyst according to claim 2, wherein the microstructures are made of metallic nickel.

4. The nano-nickel catalyst according to claim 1, wherein the metallic nickel body is spherical.

5. The nano-nickel catalyst according to claim 1, wherein the metallic nickel body is porous.

6. The nano-nickel catalyst according to claim 5, wherein the metallic nickel body is porous, and has an adsorption pore volume ranging from 0.0024 cm³/g to 0.0062 cm³/g.

7. The nano-nickel catalyst according to claim 1, wherein the metallic nickel body is solid.

8. The nano-nickel catalyst according to claim 1, wherein the metallic nickel body is hollow.

9. The nano-nickel catalyst according to claim 1, wherein the nano-nickel catalyst has a specific surface area ranging from 1.5 m²/g to 2.0 m²/g.

10. The nano-nickel catalyst according to claim 1, wherein the nano-nickel catalyst has an ability to reduce carbon dioxide into low-carbon hydrocarbons.

11. The nano-nickel catalyst according to claim 10, wherein the low-carbon hydrocarbons are selected from a group consisting of methane, ethane, propane, and a combination thereof.

12. A hydrogenation device of carbon oxides, comprising:
    a first reactor having a first catalyst bed therein; and
    a second reactor having a second catalyst bed therein, and communicated with the first reactor through a channel;
    wherein the first catalyst bed and the second catalyst bed both comprise a nano-nickel catalyst according to claim 1.

13. The hydrogenation device of carbon oxides according to claim 12, wherein the first catalyst bed has a first catalyst fill rate with a minimum value of 0.3 g/ml, and the second catalyst bed has a second catalyst fill rate with a minimum value of 0.15 g/ml.

* * * * *